(12) United States Patent
Heus et al.

(10) Patent No.: US 7,211,682 B2
(45) Date of Patent: May 1, 2007

(54) AQUEOUS SOLUTION OF A SODIUM SALT OF HEDTA

(75) Inventors: Martin Heus, Arnhem (NL); Hans Lammers, Arnhem (NL); Jim Lepage, Lima, OH (US)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 10/563,762

(22) PCT Filed: Jul. 13, 2004

(86) PCT No.: PCT/EP2004/007841

§ 371 (c)(1), (2), (4) Date: Apr. 25, 2006

(87) PCT Pub. No.: WO2005/014527

PCT Pub. Date: Feb. 17, 2005

(65) Prior Publication Data

US 2007/0015930 A1 Jan. 18, 2007

Related U.S. Application Data

(60) Provisional application No. 60/488,451, filed on Jul. 21, 2003.

(30) Foreign Application Priority Data

Jul. 30, 2003 (EP) .................................. 03077382

(51) Int. Cl.
*C07F 15/00* (2006.01)
*C07C 229/00* (2006.01)
*C09K 3/00* (2006.01)

(52) U.S. Cl. .................. 556/148; 562/565; 252/182.11

(58) Field of Classification Search ................ 556/148; 562/565; 252/182.11
See application file for complete search history.

(56) References Cited

U.S. PATENT DOCUMENTS

| | | |
|---|---|---|
| 2,893,916 A | 7/1959 | Rubin |
| 3,704,218 A | 11/1972 | Kato et al. |
| 3,767,689 A | 10/1973 | Donovan et al. |
| 3,867,419 A * | 2/1975 | Iwano et al. ................. 556/148 |
| 4,191,575 A | 3/1980 | Sykes et al. |
| 4,212,994 A | 7/1980 | Wilson et al. |
| 4,558,145 A | 12/1985 | Smith et al. |
| 4,652,350 A | 3/1987 | Cipriano et al. |
| 4,683,076 A | 7/1987 | Lampton, Jr. et al. |
| 5,091,070 A | 2/1992 | Bauer et al. |
| 5,110,965 A | 5/1992 | Thunberg et al. |
| 5,250,159 A | 10/1993 | Butterworth |
| 5,288,385 A | 2/1994 | Kedem et al. |
| 5,472,633 A | 12/1995 | Griffin, Jr. et al. |
| 5,491,259 A | 2/1996 | Grierson et al. |
| 5,898,078 A | 4/1999 | St. George et al. |
| 5,900,499 A * | 5/1999 | St. George et al. ......... 556/148 |
| 6,331,236 B1 | 12/2001 | Mani |
| 6,334,944 B1 | 1/2002 | Nambu et al. |
| 6,495,013 B2 | 12/2002 | Mazur et al. |

FOREIGN PATENT DOCUMENTS

| | | |
|---|---|---|
| DE | 21 50 994 A | 4/1973 |
| DE | 34 05 522 | 8/1985 |
| DE | 35 17 102 A | 11/1986 |

(Continued)

OTHER PUBLICATIONS

K. Nakamoto et al., *Infrared Spectra of Aqueous Solutions III Ethylenediaminetetraacetic Acid, N-Hydroxylatedelethylethylenediaminetriacetic Acid and diethylenetriaminepentaacetic Acid*, J. Am. Chem. Soc., 85, 309 (1963).

(Continued)

*Primary Examiner*—Porfirio Nazario-Gonzalez
(74) *Attorney, Agent, or Firm*—Kenyon & Kenyon LLP

(57) ABSTRACT

The invention pertains to an aqueous solution of a sodium salt $xNa^+$ $yH^+$ of the chelating compound of formula I:

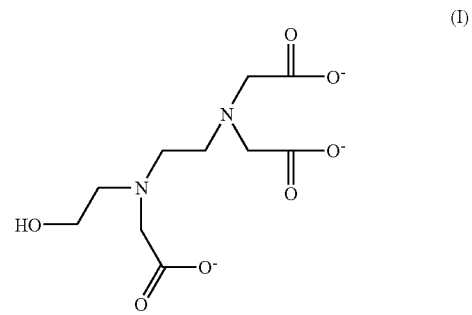

wherein $x=2.1–2.7$, $y=0.9–0.3$, and $x+y=3$. The invention further pertains to a container comprising at least 0.5 kg of said aqueous solution and to a method of preparing an aqueous solution comprising at least 45 wt % of the sodium salt $xNa^+$ $yH^+$ of the chelating compound of formula I from $Na_3$-HEDTA, comprising the steps of electrodialysing an aqueous solution containing less than 42 wt % of $Na_3$-HEDTA using a bipolar membrane, thereby converting the trisodium salt solution to the solution of the sodium salt of formula I with $x=2.1–2.7$, $y=0.9–0.3$, and $x+y=3$.

8 Claims, No Drawings

FOREIGN PATENT DOCUMENTS

| | | |
|---|---|---|
| EP | 0 054 277 A2 | 6/1982 |
| EP | 0 058 430 A1 | 8/1982 |
| EP | 0 040 254 B1 | 7/1983 |
| EP | 0 178 363 A1 | 4/1986 |
| EP | 0 205 748 | 12/1986 |
| EP | 0 184 381 B1 | 5/1989 |
| EP | 0 410 728 B1 | 1/1991 |
| EP | 0 415 119 B1 | 3/1991 |
| EP | 0 416 312 B1 | 3/1991 |
| EP | 0 471 583 A | 2/1992 |
| EP | 0 658 371 A1 | 6/1995 |
| FR | 2 822 396 A1 | 9/2002 |
| GB | 1 296 859 | 11/1972 |
| GB | 1 363 099 | 8/1974 |
| GB | 1 448 006 | 9/1976 |
| GB | 1 456 156 | 11/1976 |
| JP | 55-38305 * | 3/1980 |
| JP | 58 021 690 | 2/1983 |
| JP | 01 102 049 A | 4/1989 |
| JP | 01 284 308 A | 11/1989 |
| JP | 04 171 027 | 6/1992 |
| JP | 11 049 735 A | 2/1999 |
| RU | 2 050 176 C1 | 12/1995 |
| SU | 1 685 481 A1 | 10/1991 |
| WO | WO 91/02584 A1 | 3/1991 |
| WO | WO 96/41021 A1 | 12/1996 |
| WO | WO 99/61407 A | 12/1999 |
| WO | WO 02/48044 A2 | 6/2002 |

OTHER PUBLICATIONS

M. Bailly, *Production of Organic Acids by Bipolar Electrodialysis: Realizations and Perspectives*, Desalination, 144, 157 (2002).

P. Boyaval et al., *Concentrated Propionic Acid Production by Electrodialysis*, Enzyme Microb. Technol., 15, 683 (Aug. 1993).

National Association of Corrosion Engineers, Technical Practices Committee, NACE Standard TM-01-69, *Test Method: Laboratory Corrosion Testing of Metals for the Process Industries* (1976).

L. Bazinet et al., *Electroacidification of Soybean Proteins for Production of Isolate*, Food Technology 51(9) 52 (Sep. 1997).

* cited by examiner

AQUEOUS SOLUTION OF A SODIUM SALT OF HEDTA

The invention relates to an aqueous solution of a sodium salt of the chelating compound HEDTA [N-(2-hydroxyethyl) ethylenediamine-N,N',N'-triacetic acid], to a container comprising said aqueous solution, and to the use thereof for making an iron-chelate complex. The invention further relates to a method for preparing such an aqueous solution of said sodium salt of HEDTA.

Some sodium salts of the chelating compound HEDTA are known in the art. For instance, in U.S. Pat. No. 5,491,259 a method is disclosed for preparing HEDTA from the trisodium salt thereof (i.e. $Na_3$-HEDTA). This method makes use of an acidic medium at pH 1.0 to 3.0, resulting in an aqueous feed solution containing fully protonated HEDTA along with an inorganic sodium salt. Subsequently, this aqueous solution is passed through a diafiltration membrane to separate the organic and inorganic components.

The disodium salt of HEDTA (i.e. $Na_2$-HEDTA) is also known. For instance, in EP 0 054 277 and EP 0 058 430 microscopic capsules containing dyestuff suspensions with said disodium salt of HEDTA were disclosed. K. Nakamoto et al. published the infrared spectra of HEDTA, and its mono-, di-, and trisodium salt in *J. Am. Chem. Soc.* 85, 311–312 (1963).

Commonly, when using HEDTA for chelating ions, the trisodium salt of HEDTA ($Na_3$-HEDTA) is used. Thus, according to U.S. Pat. No. 5,110,965 iron chelates can be made from a commercially available 41.3 wt % aqueous solution of the trisodium salt of HEDTA by reacting an oxide of iron (as its magnetite) with $Na_3$-HEDTA and acidifying the medium to a low pH value.

However, the use of the trisodium salt of HEDTA has some major drawbacks when used on a commercial scale. An important problem is the high viscosity of concentrated solutions of the trisodium salt of HEDTA, which makes such a solution difficult to handle. Thus, the high viscosity limits the practical concentration to values below 45 wt %. Further, above certain concentrations, the trisodium salt of HEDTA tends to precipitate from the aqueous solution when being exposed to lower temperatures, making it necessary to heat the containers before the solution can be poured out. It was further found that aqueous $Na_3$-HEDTA solutions are corrosive to aluminum and therefore limits its application to corrosive-proof installations. These problems become particularly relevant when using HEDTA salt in large-scale productions, thus especially when containers with a content of 0.5 kg or more are used. In practice containers can contain 25 to 1,000 kg of aqueous HEDTA salt, or even more.

It is an objective of the present invention to provide an alternative for the aqueous solutions of the trisodium salt of HEDTA that has lower viscosity, does not precipitate at low temperature, can be handled in containers at higher concentrations, and has less corrosive properties.

The instant invention provides aqueous solutions of sodium salts of HEDTA satisfying the above conditions. To this end it was surprisingly found that the above-mentioned problems do not occur with an isolated aqueous solution of a sodium salt $xNa^+$ $yH^+$ of the chelating compound of formula I:

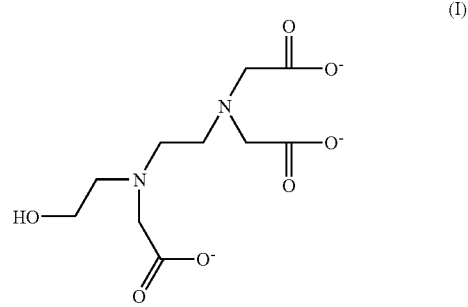

wherein $x=2.1–2.7$, $y=0.9–0.3$, and $x+y=3$.

Furthermore, the present invention provides containers comprising at least 0.5 kg of an aqueous solution of said sodium salt of HEDTA, since it was found that the above-mentioned problems do not occur in containers comprising at least 0.5 kg of said solution. The term "container" as used throughout this specification is not only meant to include reservoirs in which the sodium salt of HEDTA according to the present invention can be stored and/or transported, but also tanks, barrels, drums, vessels, pipes or flush lines which can contain said sodium salt and which are used in a production process. The containers of the invention contain at least 0.5 kg of the above solution, preferably at least 1 kg, and most preferably 25 kg or more. Preferably, said containers do not contain more than 2,000 kg, more preferably 1,500 kg of the above solution. Preferably, the containers comprising at least 0.5 kg of the aqueous solution according to the present invention are made of PVC, polyethylene, stainless steel, or bituminized steel.

In order to use as less as possible acid for neutralization it is preferred to make an aqueous solution that is as close as possible to the trisodium salt, without having the disadvantages of the trisodium salt. It was found that an optimum regarding the use of neutralization acid, viscosity, precipitation and corrosive properties was obtained for x is about 2.4, for instance within the range 2.3 to 2.5.

It was furthermore found that the salt of the invention could be dissolved in water to a concentration of 45 wt % or higher without impairing the hereinbefore-mentioned advantages. To satisfy the above conditions the aqueous solution has a pH between 7 and 11.

In another objective according to the invention there is provided in a use of the aqueous solution comprising the sodium salt $xNa^+$ $yH^+$ of the chelating compound of formula I, wherein $x=2.1–2.7$, $y=0.9–0.3$, and $x+y=3$, for preparing an iron-chelate complex. The preparation of this type of complex as such is known in the art, for instance as indicated above in U.S. Pat. No. 5,110,965. When applying the aqueous HEDTA salt of the present invention, it is further clear to the skilled man how to make such complexes. Other metals than iron can also be complexed, such as other Group VIII metals, transition metals, rare earth metals, and the like. If Fe complexes are made, the aqueous HEDTA salt solution preferably contains 5–7 wt % of the iron complex.

It is also an object of the invention to provide a method for making the above-mentioned aqueous HEDTA salt solutions. To this end the invention pertains to a method of preparing an aqueous solution comprising at least 45 wt % of the sodium salt $xNa^+$ $yH^+$ of the chelating compound of formula I wherein $x=2.1–2.7$, $y=0.9–0.3$, and $x+y=3$ from the trisodium salt of N-(2-hydroxyethyl)ethylenediamine-N, N',N'-triacetic acid ($Na_3$-HEDTA), comprising the step of electrodialysing at ambient temperature, i.e. 20° C., an aqueous solution containing less than 42 wt % of $Na_3$-HEDTA, or at a different temperature at maximally the concentration whereby the viscosity is the same or lower than the viscosity of the 42 wt % $Na_3$-HEDTA solution at 20° C. using a bipolar membrane and a cation exchange membrane, thereby converting the $Na_3$-HEDTA solution into the solution of the sodium salt $xNa^+ yH^+$ of formula I with x=2.1–2.7, y=0.9–0.3, and x+y=3.

Electrodialysis processes with bipolar membranes (EDBM) are known in the art. An overview of such processes can be found in M. Bailly, *Desalination*, 144, 157–162 (2002). When using such process for making the sodium salt of HEDTA according to the present invention, preferably a caustic electrolyte is used, such as sodium or potassium hydroxide, sodium (hydrogen) carbonate, and the like. Suitable bipolar membranes are for instance Neosepta® BP1 E from Tokuyama Corporation Ltd. (Japan), FT-BP™ from FumaTech GmbH (Germany) or Morgane® BPM from Solvay (Belgium). A cation exchange membrane is used to separate the acid compartment from the base compartment and also to transport the sodium ions from the acid to the base compartment. Cation exchange membranes for this application should be acid and base stable. Suitable cation exchange membranes are for instance Neosepta® CMB (Tokuyama Corp.), FT-FKL™ and FT-FKB™ (both FumaTech GmbH) but any other cation exchange membranes can be used as long as these are acid and base stable and stable in the HEDTA solution under the conditions of the electrodialysis process.

The higher the temperature during electrodialysis, the lower the viscosity of the $Na_3$-HEDTA solution. Thus, when higher temperatures are selected, higher concentrations than 42 wt % of $Na_3$-HEDTA can be used. However, when the viscosity of the solution becomes higher than the viscosity of a 42 wt % solution at 20° C., i.e. higher than about 25 cPoise, the transport of such a solution through the thin channels of electrodialysis cells is in general too much hampered to obtain an efficient process. It is therefore preferred to work at temperatures high enough to ensure that the viscosity is not higher than about 25 cPoise, but low enough to ensure that the membranes can still operate properly. When heat sensitive membrane types are used, the electrodialysis process is preferably performed at lower temperatures, down to room temperature.

The bipolar membrane electrodialysis process can be operated up to 90° C., which is the maximum temperature which most of the cation exchange membranes can stand. Preferably, the temperature should be below about 60° C. when applying the FumaTech FT-BP™ or Morgane® BPM from Solvay bipolar membranes or below about 45° C. when applying the Tokuyama Corp. Neosepta® BP1 E bipolar membrane. From a practical point of view the process is most preferably performed at a temperature between 20 and 45° C.

It is noted that due to electro-osmosis, water together with the sodium ions migrates from the HEDTA compartment through the cation exchange membrane into the caustic compartment. The HEDTA concentration therefore increases during the acidification process.

It is furthermore noted that, although less preferred, the aqueous solution comprising at least 45 wt % of the sodium salt $xNa^+ yH^+$ of the chelating compound of formula I wherein x=2.1–2.7, y=0.9–0.3, and x+y=3, can also be prepared from $Na_3$-HEDTA by means of an electrolysis process comprising an electrochemical acidification step as for example described by P. Boyaval, J. Seta, and C. Gavach in *Enzyme Microb. Technol.*, 1993, Vol. 15, August, p. 683–686.

The invention is further illustrated with the following examples.

EXAMPLE 1

A $Na_3$-HEDTA solution with pH 11.05 and having a concentration of 41 wt % of $Na_3$-HEDTA expressed as a Fe-TSV value (Iron Total Sequestering Value) was converted to the sodium salt $xNa^+ yH^+$ of the chelating compound of formula I wherein x=2.1–2.7, y=0.9–0.3, and x+y=3 by circulating the solution through a bipolar membrane (Neosepta® BP1; ex Tokuyama Corporation Ltd.) electrodialysis stack using a conventional pump. Due to the heat produced during the acidification process, the temperature of the HEDTA sodium salt solution increased from 30° C. at the start of the experiment to 45° C. at the end of the experiment. During the experiment, the pH-value in the HEDTA compartment was measured using a conventional calibrated pH-meter with a combined glass electrode. During acidification using said bipolar membrane electrodialysis stack, the pH-value of the HEDTA sodium salt solution decreased. It was found that when the pH had reached a value of 9.6 at a temperature of 35° C., the fluid flow of the HEDTA sodium salt solution, which was measured using a conventional flow meter, started to increase sharply from 40 l/h to over 200 l/h without changing the pump settings and/or other conditions. This indicates that the viscosity of the HEDTA sodium salt solution at the said conditions decreases sharply. The final HEDTA sodium salt solution that was obtained had a pH of 9.1, which corresponds with the sodium salt $xNa^+ yH^+$ of HEDTA wherein x=2.7 and y=0.3. The viscosity of said final solution measured with a Brookfield viscosity meter was 16.2 cPoise at 20° C. and 7.7 cPoise at 50° C.

EXAMPLE 2

Sodium salts $xNa^+yH^+$ of the chelating compound of formula I having various x and y values were prepared by acidification using the bipolar membrane electrodialysis stack as described in Example 1, until the desired pH value was obtained. The viscosity of the thus obtained HEDTA solutions was measured over a wide range of concentrations at two different temperatures (20° C. and 50° C.) using a Brookfield viscosity meter.

The Tables below show the viscosity (centiPoise) against HEDTA concentration (as Iron Total Sequestering Value, Fe-TSV, expressed as $Na_3$-HEDTA salt) for the $xNa^+ yH^+$ salt of formula I in which x=3 (comparative example), x=2.4, and x=2.1, and y=0, y=0.6, and y=0.9, respectively.

TABLE I

Viscosity of HEDTA salts in relation to Fe-TSV at 20° C.

| Concentration (wt %) | x = 3 viscosity (cP) | x = 2.4 viscosity (cP) | x = 2.1 viscosity (cP) |
|---|---|---|---|
| 10 | 2 | 2 | 2 |
| 30 | 7.1 | 5.2 | 4.3 |
| 40 | 19 | 12.7 | 10 |
| 50 | ∞* | 54 | 32.9 |

*The viscosity of $Na_3$-HEDTA at 50 wt % could not be determined due to solidification of the product.

At low concentration (10 wt %) there was no significant difference measured in the viscosity between $Na_3$-HEDTA (prior art) and $Na_{2.4}$-HEDTA and $Na_{2.1}$-HEDTA (this invention). At higher concentrations the viscosity differences became large. At 50 wt % $Na_3$-HEDTA could not be used anymore because it solidified, whereas both $Na_{2.4}$-HEDTA and $Na_{2.1}$-HEDTA could still easily be handled.

TABLE II

Viscosity of HEDTA salts in relation to Fe-TSV at 50° C.

| Concentration (wt %) | x = 3 viscosity (cP) | x = 2.4 viscosity (cP) | x = 2.1 viscosity (cP) |
|---|---|---|---|
| 10 | 1 | 1 | 1 |
| 30 | 3.1 | 2.3 | 2.3 |
| 40 | 6.7 | 5.2 | 4.2 |
| 50 | 21.1 | 14.2 | 10.1 |

At higher temperature (50° C.) the viscosity differences between $Na_3$-HEDTA (prior art) and $Na_{2.4}$-HEDTA and $Na_{2.1}$-HEDTA, although smaller than at 20° C., remained.

The advantages of low viscosity are that it is easier to empty drums/containers, flush lines, maintain flows during pumping/handling the product, etc.

EXAMPLE 3

Transport classification of aqueous HEDTA solutions is also linked to corrosive potential. Corrosion tests carried out according to the NACE standard TM-01-69 using a 40 wt % caustic-free $Na_3$-HEDTA solution on aluminum 7075 T6 showed that the rate of corrosion to aluminum was above the allowed limit (max. average corrosion rate of 6.2 mm/year). This test with a 40 wt % $Na_{2.3}H_{0.7}$-HEDTA aqueous solution gave an average corrosion rate for aluminum 7075 T6 of <1 mm/year. This allows the product to be handled in aluminum containers and production equipment.

The invention claimed is:

1. An aqueous solution comprising a sodium salt $xNa^+ yH^+$ of the chelating compound of formula I:

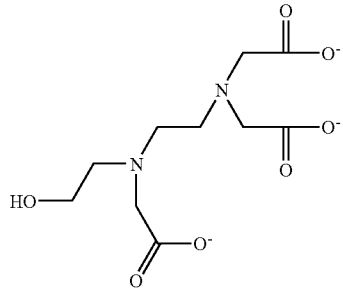

wherein x=2.1–2.7, y=0.9–0.3, and x+y=3.

2. The aqueous solution according to claim 1 comprising at least 45 wt % of the sodium salt $xNa^+yH^+$ of the chelating compound of formula I wherein x=2.1–2.7, y=0.9–0.3, and x+y=3.

3. A container comprising at least 0.5 kg of an aqueous solution according to claim 1.

4. A method for preparing an iron-chelate complex, comprising: contacting the aqueous solution according to claim 1 with an iron-containing material.

5. A method of preparing an aqueous solution comprising at least 45 wt % of the sodium salt $xNa^+yH^+$ of the chelating compound of formula I according to claim 1 wherein x=2.1–2.7, y=0.9–0.3, and x+y=3 from the trisodium salt of N-(2-hydroxyethyl)ethylene-diamine-N,N',N'-triacetic acid ($Na_3$-HEDTA), comprising the step of electrodialysing at 20° C. an aqueous solution containing at least 42 wt % of $Na_3$-HEDTA, or at a different temperature at maximally the concentration whereby the viscosity is the same or lower than the viscosity of 42 wt % $Na_3$-HEDTA solution at 20° C., using a bipolar and a cation membrane, thereby converting the $Na_3$-HEDTA solution to the solution of the sodium salt $xNa^+yH^+$ of the chelating compound of formula I according to claim 1 wherein x=2.1–2.7, y=0.9–0.3, and x+y=3.

6. The method according to claim 5 wherein a caustic electrolyte is used.

7. A container comprising at least 0.5 kg of an aqueous solution according to claim 2.

8. A method for preparing an iron-chelate complex, comprising: contacting the aqueous solution according to claim 2 with an iron-containing material.

* * * * *